United States Patent [19]

Storace et al.

[11] Patent Number: 4,582,237
[45] Date of Patent: Apr. 15, 1986

[54] SURGICAL STAPLING SYSTEM, APPARATUS AND STAPLE

[76] Inventors: Anthony Storace, 46 Princes Pine Rd., Norwalk, Conn. 06850; Paul R. Sette, 94 Edgecomb St., Hamden, Conn. 06517

[21] Appl. No.: 526,777

[22] Filed: Aug. 26, 1983

[51] Int. Cl.$^4$ .............................................. A61B 17/04
[52] U.S. Cl. ................................. 227/19; 128/334 R; 227/DIG. 1
[58] Field of Search ............. 128/334 R; 227/DIG. 1, 227/19, 83, 756, 720

[56] References Cited

U.S. PATENT DOCUMENTS

| | | | |
|---|---|---|---|
| 3,665,924 | 5/1972 | Noiles et al. | 227/DIG. 1 |
| 3,945,238 | 3/1976 | Eckert | 227/DIG. 1 |
| 4,396,139 | 8/1983 | Hall et al. | 227/19 |
| 4,399,810 | 8/1983 | Samuels et al. | 227/19 X |
| 4,411,378 | 10/1983 | Warman | 227/19 |

*Primary Examiner*—Paul A. Bell
*Attorney, Agent, or Firm*—J. David Dainow

[57] ABSTRACT

A surgical stapler having a pivotable trigger in a housing and a cartridge of surgical staples, has a moving anvil which receives one staple at a time in its open configuration. A forming blade moves to engage and capture the staple between the forming blade and the anvil and drive the staple away from the cartridge allowing the user to see and place the points of the staple at a desired location on the tissue. Further movement of the forming blade pressing upon the top of the staple forces the staple legs to pierce and close joining adjacent edges of tissue. A detent prevents reversibility of the trigger and return of the staple after and the trigger reaches a pre-cock position, allowing the user to relax his hand while the staple remains exposed, until the trigger stroke is completed and the staple is closed and stripped from the anvil.

30 Claims, 22 Drawing Figures

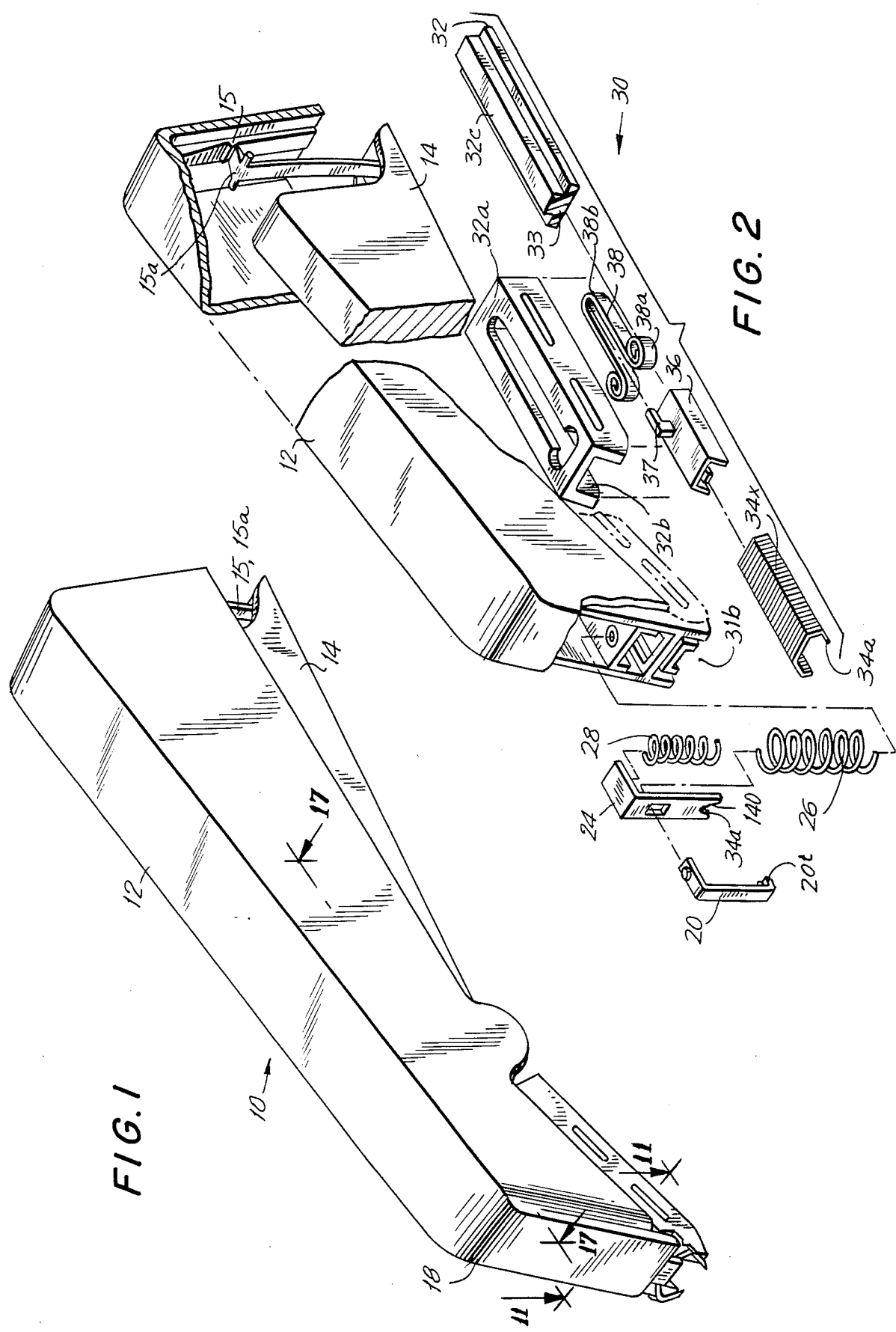

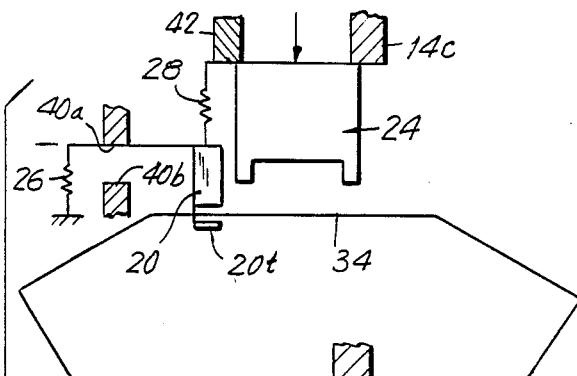
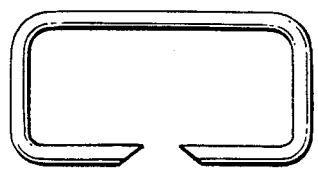
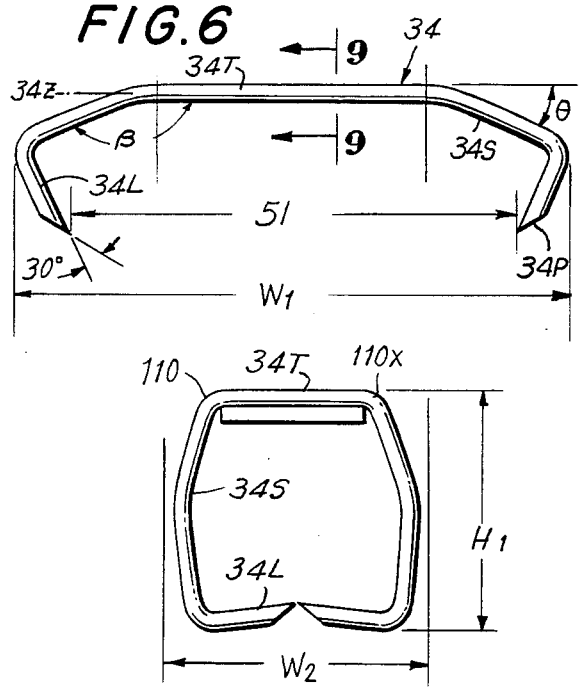
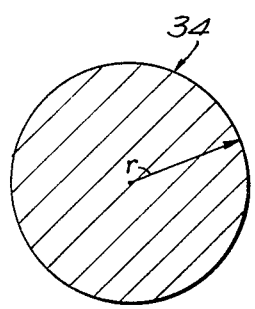
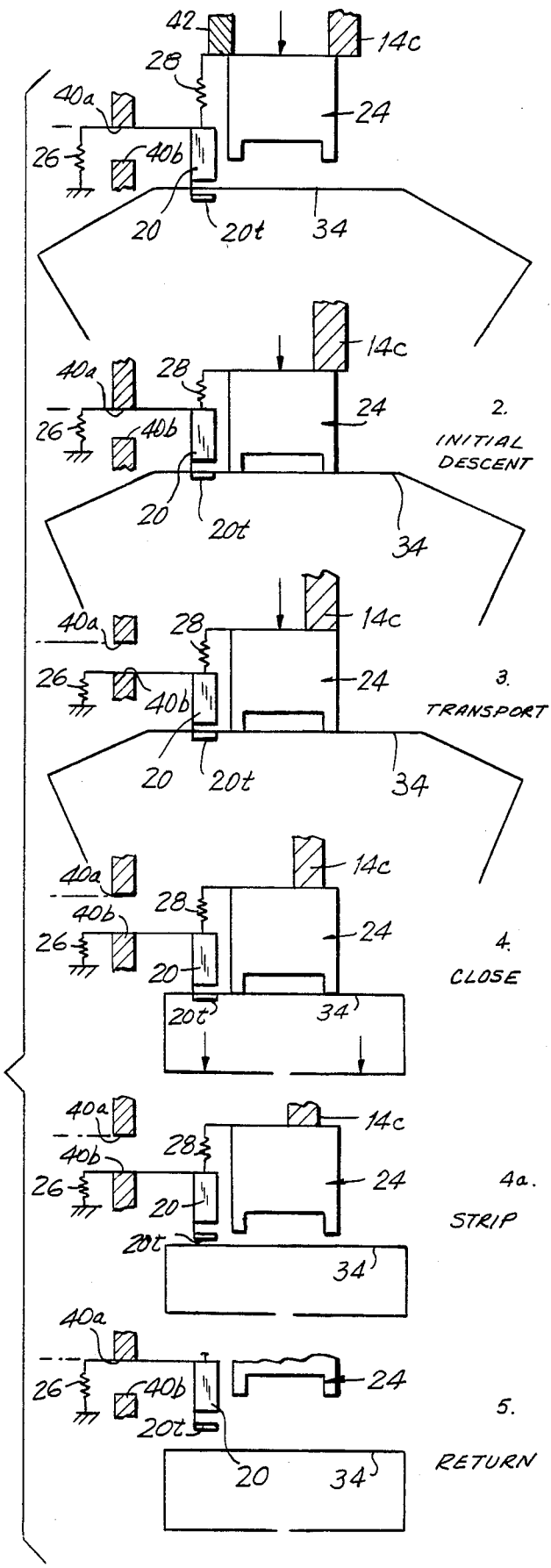

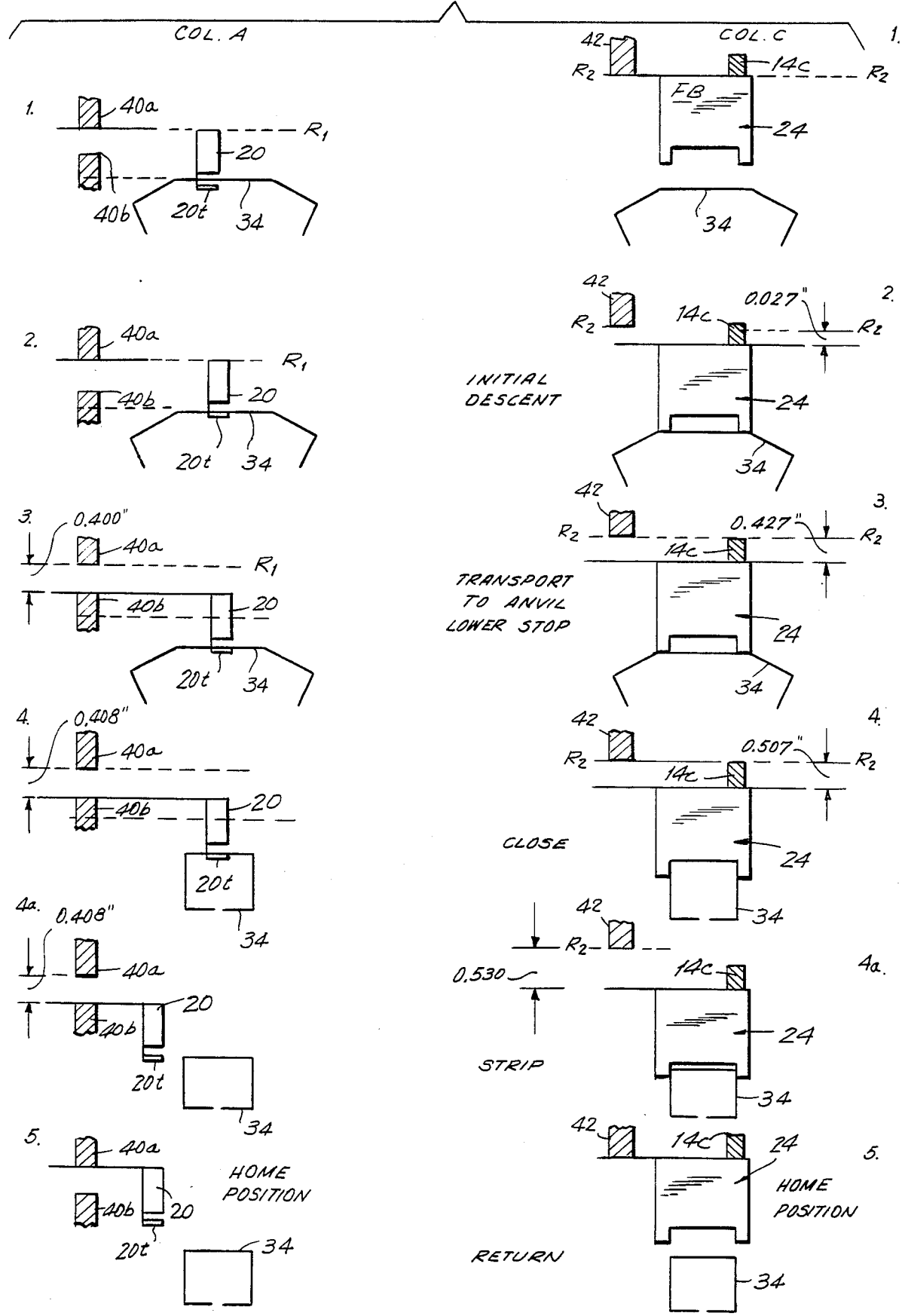

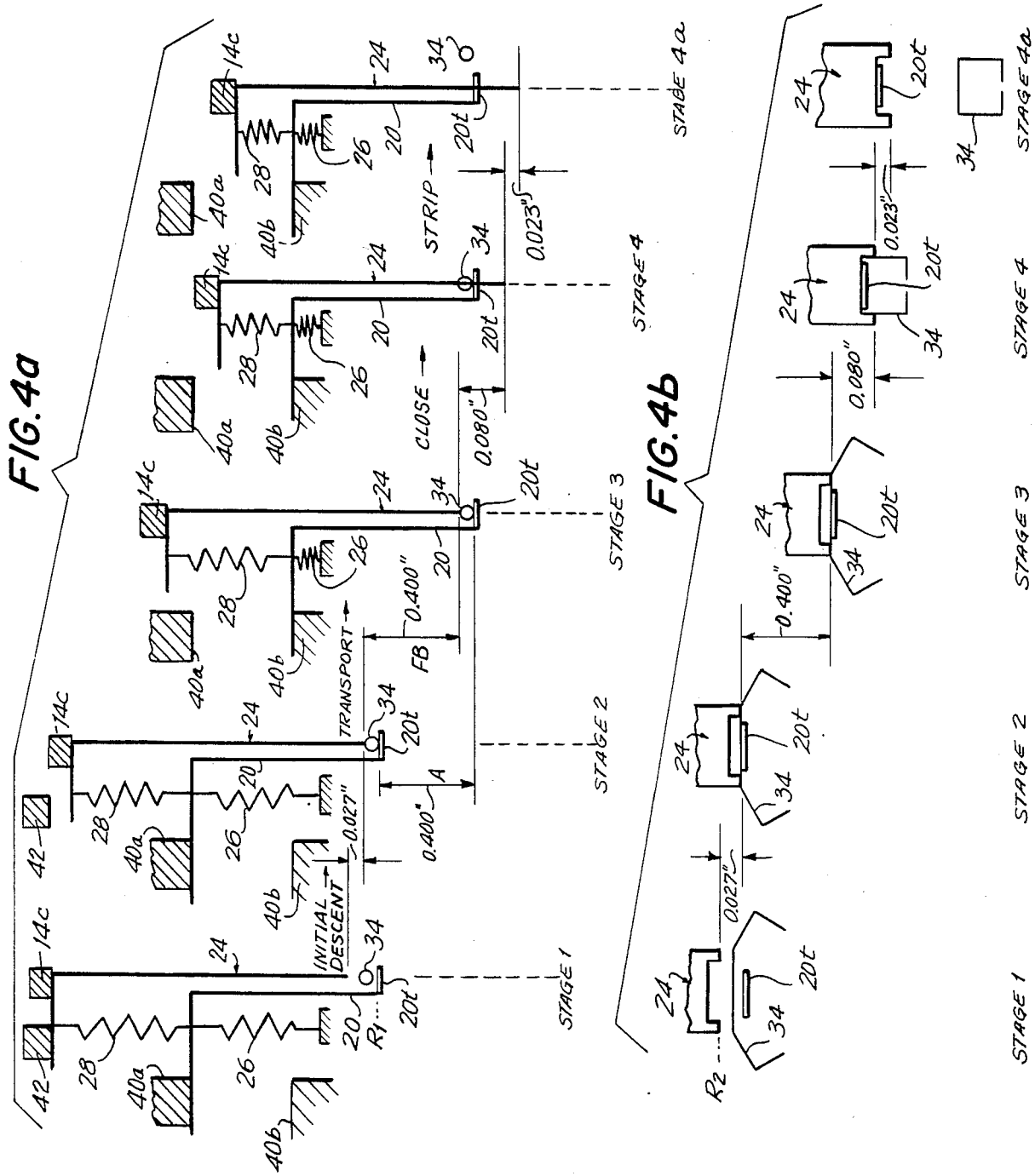

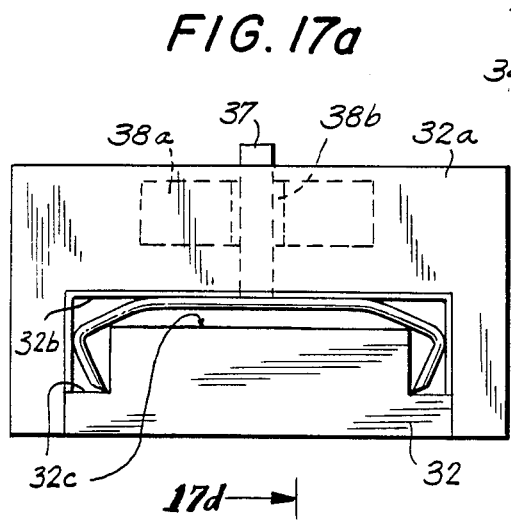
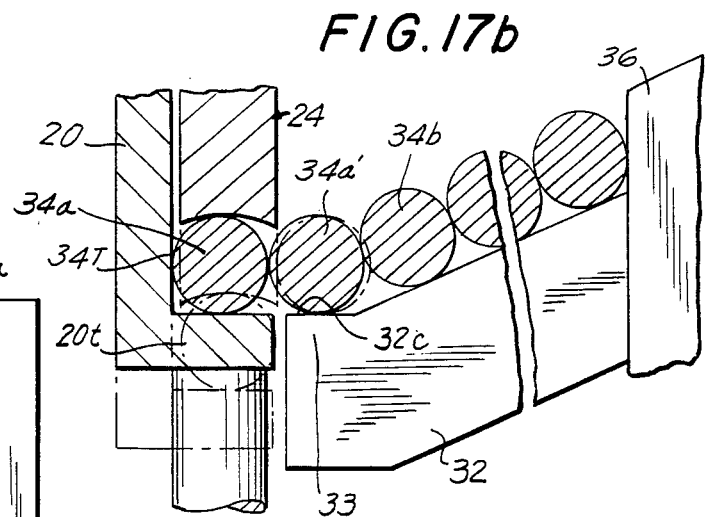
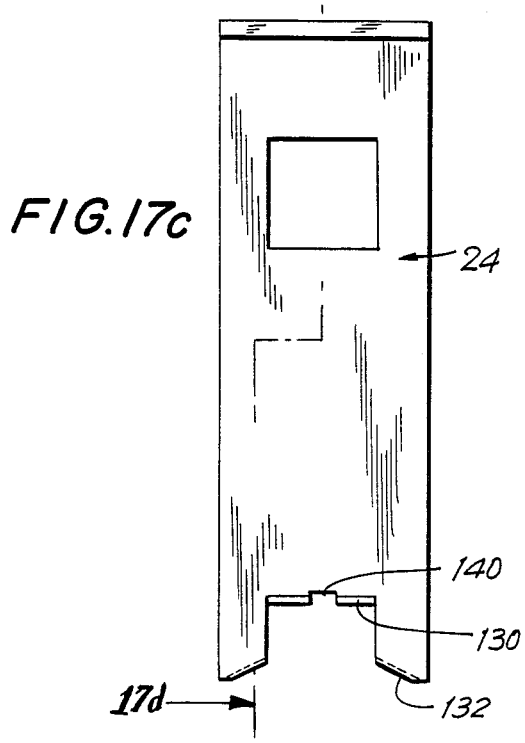
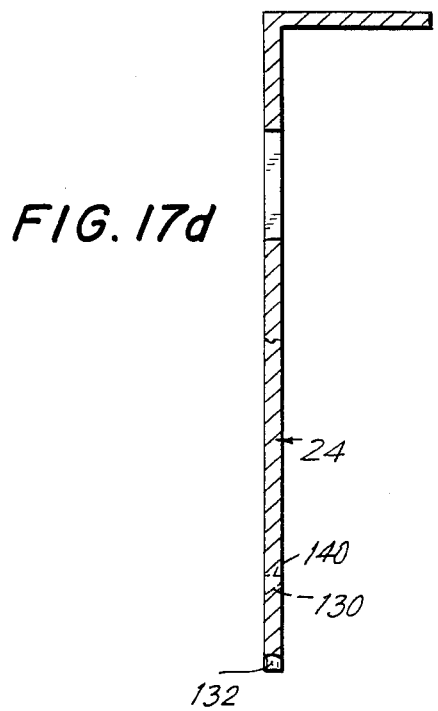
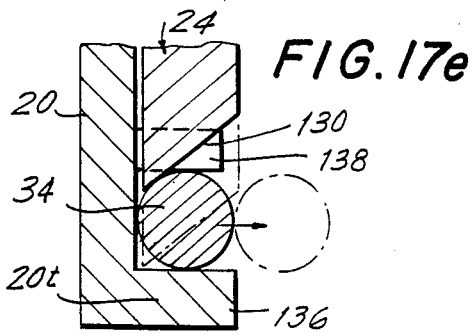
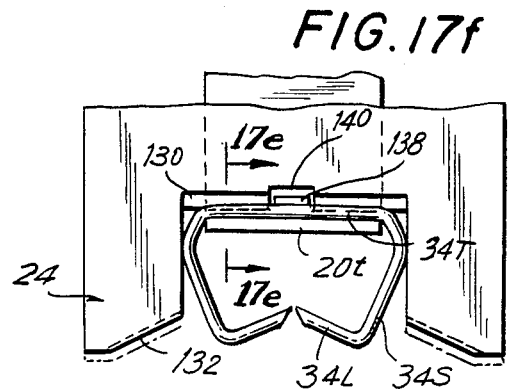

SURGICAL STAPLING SYSTEM, APPARATUS AND STAPLE

BACKGROUND OF THE INVENTION

This invention is in the field of surgical staples and surgical staple guns for implanting such staples. A very large number of surgical stapler devices have been made in the last few years by a growing number of manufacturers; however, in all cases the staples used were essentially conventional stainless steel or equivalent staples, generally similar to those used for stationery products, other packaging or joining equipment. More particularly such staples are preformed in a wide open condition with legs of the staple directed parallel and downward from a top arch or crossbar to grasp adjacent edges of an incision for closure. These staples are contained in a magazine, and each is released one at a time and moved laterally forward to a fixed anvil which supports the underside of the crossbar while its sharply pointed ends engage and pierce tissue and are forcibly bent to close about and capture the edges of the juxtaposed tissue.

In typical prior art staplers the staple is forced from a generally rectangular configuration to generally closed rectangular configuration by applying force at two points on the top side of the staple while restraining it inbetweeen these points. The term anvil is used because the staple is closed by forcing the legs against a fixed, rigid anvil-like support within or near the surface of the stapler's housing. Such substantial forces are required that the support anvil is traditionally a fixed portion of the housing, which thus results in the staple being implanted and closed while its upper arch part remains in the stapler. This arrangement obviously has a limiting effect on the surgeon's ability to see the stapler and the wound.

In addition to the visibility limitation due to the location of the staple partially within the device during closure, the prior art devices are relatively large to begin with which is another inherent visibility obstacle. The width dimension of the prior art housing, for example, must be at least equal to the width of a staple in its fully open configuration in the staple magazine, plus housing thickness and clearance, this total width dimension being significantly greater than the width of a staple in closed configuration.

SUMMARY OF THE INVENTION

This invention is a new surgical staple and a stapler designed to deliver and implant a plurality of staples, one at a time into a patient's tissue, specifically to engage adjacent edges of an incision or wound and close in a manner to hold together these edges. The staples typically made of stainless steel define a wide angular C-shape with two sharply pointed ends directed generally downward and inclined slightly toward each other when the staple is in open condition. When closed each staple has a generally rectangular shape with the legs directed at each other and optionally inclined slightly upward to provide a highly secure closure.

Principal objectives in the present invention are to provide an apparatus which is extremely simple and reliable in operation, one which is simple and inexpensive to manufacture by having the fewest possible parts that can be assembled rapidly, and, furthermore, one which provides high visibility in the area of the staple discharge from the gun so the surgeon can see the staple as he positions it prior to closure and during closure. The new device closes each staple with ample force to pierce skin consistently and reliably, yet requires less force by hand to do so. When closed the staple has its pointed ends either slightly upward or overlying or at least very close together. Also the invention includes a "feelable" pre-cock position at which point a detent engages and prevents return of the trigger. The surgeon can release his hand while the staple is held in its pre-cock position. Furthermore, the device has a non-directional staple release function; accordingly there is no need to move the gun forward, backward, upward or downward to effect release of the closed staple from the gun.

Basically, this surgical stapler is a hand device with a handle part which is gripped in the surgeon's palm and a pivotal or otherwise movable trigger part which is moved when squeezed by the surgeon's fingers against the adjacent handle. The trigger is an elongated element with a pivot point close to the front end so that movement of one end causes opposite motion of the remote end. A mainspring is situated in the housing to urge a forming element upward to bear against and urge the trigger to a clockwise or open position within the handle. Within the stapler the trigger, driven by the surgeon's hand, is the basic power source which is transmitted through various components to deliver and close each staple.

Also inside the device is a magazine containing a plurality of staples arranged in a generally traditional manner, aligned on a magazine mandrel or core and urged by independent spring means to slide along and then off the mandrel one at a time. Obviously, the device allows only the outermost staple to be discharged to a descending anvil and driver element for descent to the discharge area below the cartridge where the staple is closed. The driver or forming blade and moving anvil comprise a sub-assembly for engaging, stabilizing, restraining, delivering the staple to a lower level, closing and finally releasing the staple. An objective is for the separation of the staple from the staple gun to occur easily, quickly and smoothly without further movement of the gun relative to the wound and without chance of the staple "hanging-up" in the gun. When so closed and released the staple is outside of and partially or totally below the cartridge or magazine and lower portion of the gun.

In our preferred embodiment the new staples are stored in the cartridge in the stapler in partially closed state; the resulting housing thus occupies less width than prior art housings and thus provides improved visibility at the closure area. The staple is delivered to a point below the cartridge.

In the new stapler means are provided on the forming blade for preventing the staple from tipping and rolling out of its generally vertical plane. Associated with the forming blade are stripper means for stripping or prying a closed staple off of the anvil so that the stapler device can be easily and smoothly separated from the closed and emplaced staple.

It should be noted that the design of this stapler requires that the trigger be squeezed from open to closed position through a series of phases during which the staple goes through its complete cycle of: engagement, descent, pre-cock, tissue engagement, pierce tissue of opposed edges of the incision, close, and finally separate from the gun. It is the intent herein that the gun and its trigger move in one consistent direction during the entire staple formation and movement phase. This is logically consistent, adds to overall simplicity of the device, and is helpful psychologically for the user to have a trigger moving in only one direction to complete all phases of the staple manipulation to close. This "forward" motion is reversible until the pre-cock position is reached.

By having the staple positioned below the cartridge and in front of the tapered housing, the surgeon can clearly see precisely where the pointed ends of the legs of the staple will be engaged in the tissue. Not only does the new device permit these totally new and novel operations with staples, it does so with the highest visibility ever achieved because the staple, during these moments of final decision, is fully exposed and essentially out of the stapler while it is held by the staple engaging means.

A further feature of one embodiment of this device is the incline of the staple magazine so that the lower housing will be smaller and allow for greater visibility. As generally indicated, the magazine is aligned along an axis that defines an angle less than 90° with the line of descent of the staple driver. It has been found possible to incline the line of descent of the staples relative to the magazine.

In a preferred embodiment the drive system for engaging, transporting, closing and releasing each staple is basically a handle or trigger with a pivot point nearer to one end such that an approximately 3 to 1 leverage ratio is established, and so that a 20° pivot movement of the trigger's near end by the surgeon's hand will cause the remote end by direct linkage to actuate and drive the remaining components i.e. the forming blade moves sequentially between its start, engage, transport, close and release or strip positions. Alternative drive mechanisms could include gear trains and cam-follower arrangements for producing linear movement of the staple driver from pivoting or other movement of the surgeon's hand.

As described generally above, each staple goes through engagement, descent, closing and release. In a cam drive system, different cams can easily accomodate these different take-offs while the trigger is pivoted smoothly and/or continuously. In direct drive mechanisms means are provided to allow the trigger's continuous pivoting to cause staple-engaging and forming means to first drive a staple downward from the magazine, and then to close and release the staple. Closing of the staple while it remains at a lower elevation requires an "idling" phase of the anvil while the trigger continues moving. This is an accomplished in one embodiment by using relatively soft and hard springs axially, the latter not moving until the former is fully compressed.

A variety of other and specific features are disclosed in the detailed drawings and descriptions that follow of preferred embodiments of carrying out the principles of this new stapler invention.

BRIEF DESCRIPTION OF THE DRAWINGS

FIG. 1 is a front perspective view of the new surgical stapler.

FIG. 2 is an exploded view of the stapler of FIG. 1.

FIG. 3 is a schematic representation of the forming blade, anvil and staple elements in their sequential phases of operation.

FIG. 4 is a schematic representation corresponding to FIG. 3 showing separated sub-assemblies.

FIG. 4a and 4b show lateral spread views of FIG. 4.

FIG. 5 is a front elevation of a prior art staple in closed state.

FIG. 6 is a front elevation of a new staple in open state.

FIG. 7 is a front elevation of the staple of FIG. 6 in closed state.

FIG. 9 is a typical cross-sectional view of the staple, this taken along line 9—9 of FIG. 6.

FIG. 17A is a front elevation view of the staple magazine.

FIG. 17B shows a detail side elevation view partly in section of staples moving from the magazine to the anvil and forming blade.

FIG. 17C shows a rear elevation view of the forming blade.

FIG. 17D shows a cross-sectional view of FIG. 17C.

FIG. 17E shows a detail view of the stripper of FIGS. 17A and 17C.

FIG. 17F shows a rear elevation of FIG. 17E.

FIG. 18 is a fragmentary view similar to FIG. 17 with the stapler descended.

DETAILED DESCRIPTION OF THE PREFERRED EMBODIMENT

Figure 19A:
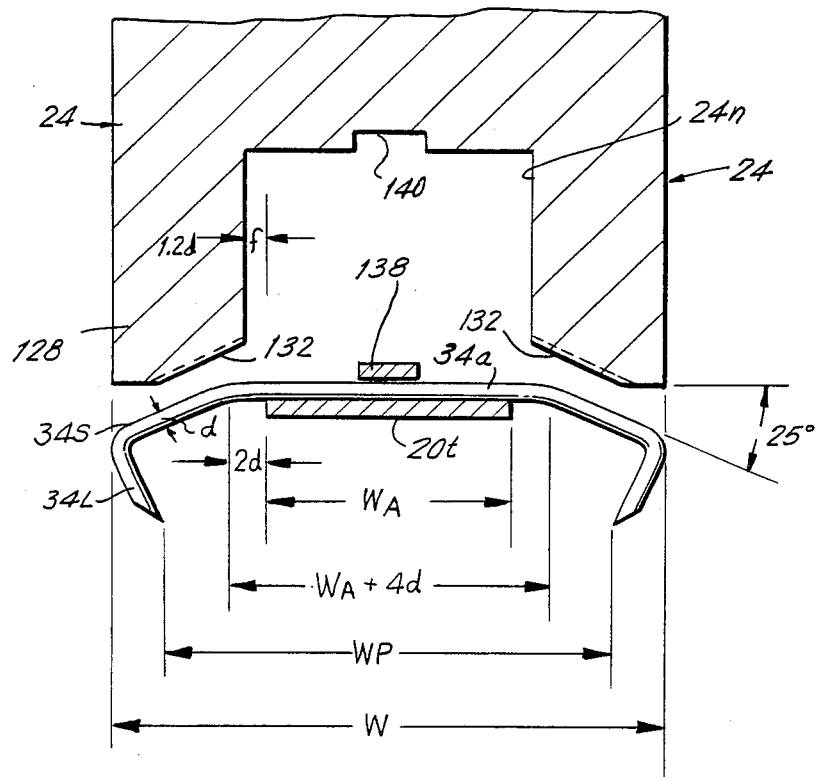
FIG. 19A is a fragmentary sectional view of the staple-forming sub-assembly correspoding to FIGS. 19 and 17f.

The new surgical stapler is illustrated in FIG. 1 showing an assembled device and in FIG. 2 which is an exploded view showing its various principal components. As illustrated in these figures the stapler assembly 10 has a casing or housing 12 with a trigger 14 which is pivotable within the casing about pivot 16, and a detent and spring clip combination 15, 15a to provide an audible and/or physical indication that closure of a staple is imminent and to prevent reversibility once engaged. At the front of the stapler is a front cover portion 18 of the casing 12 in the area where staples are discharged one at a time. A cartridge assembly or magazine 30 holds a plurality of staples 34x on a mandrel 32; a pusher 36 driven by a pusher spring 38 urges the staples toward the left as shown. The magazine is inserted into the stapler casing with staples at the front end 33 of the mandrel 32 situated near the front opening 31b of the casing 12. The lead staple 34a of the plurality of aligned staples 34x would be pushed outward into the staple-forming sub-assembly. Generally stated, one staple at a time is discharged into the forming blade anvil sub-assembly which, upon squeezing of the trigger, then lowers the staple below the lower front part of the casing. Further squeezing of the trigger closes the staple and finally releases the staple from the device, all these phases being illustrated schematically step-by-step in FIGS. 3 and 4.

The illustrations of staples in the different figures vary as follows: FIG. 5 shows a prior art staple; FIGS.

6, 7, 19, 20, 2, 19a, and 17a show the new staple intended to be used with the new stapler of this invention; FIGS. 3, 4, 4a and 4b show the new staple in schematic representations which in some instances differ from actual appearance of the staple in order to better demonstrate function.

The staple-forming sub-assembly as seen in FIG. 2, 19a and 17-17f comprises the anvil 20 for receiving the lead staple, and the forming blade 24 for driving the staple downward and closing the staple. Anvil spring 26 urges the anvil to its normally upward position, and forming blade spring 28 urges the forming blade also upward relative to the anvil and relative to the casing. An additional feature, particularly shown in FIGS. 17c-17f in the stripper 130 portion of the forming blade which strips or separates a closed staple from the staple-forming subassembly, so that the stapler can be removed from such closed staple which is embedded in a patient's tissue.

The lead staple 34a in the staple magazine is received upon the lower lip 20t of the anvil 20, and subsequently held between said lip and the bottom edge of the forming blade 24. Next the forming blade is driven further downward against the top of the staple's crossbar or arch, which along with the anvil is pushed downward until the anvil is stopped, and the forming blade continues its descent relative to the staple which is supported in place by the anvil. As a result, the forming blade forces the partially open leg parts of the staple to be closed for joining and holding adjacent edges of the tissue.

In the cartridge or magazine assembly 30 illustrated in FIG. 2 the staples 34x and pusher 36 slide along the top of mandrel 32 while spring 38 is situated with its ends 38a secured to the front of the mandrel and its mid-part positioned to engage the rear side of the pusher's upward extending tab 37. This spring is preferably a Negator ® spring applying constant tension regardless of the amount of extension of the spring which will vary depending on the number of staples remaining in the cartridge, to urge the staples off the mandrel in a direction toward the left as shown. The pusher 36 has its own tang (not shown) which projects outward through the housing; the position of this tang indicates the axial position of the pusher and thus the approximate number of staples remaining in the magazine.

The operational phases of the staple-forming assembly are shown schematically in FIGS. 3, 4 and 4A and 4B. The phases are designated 1, 2, 3, 4, and 4a, after which the cycle is repeated as indicated by phase 5. Phase 4A is shown for the strip-off operation wherein the staple is separated from the device. FIG. 3 is a schematic view showing all the principal elements at once which are indicated by reference numerals corresponding to those in the exploded view of FIG. 2. Accordingly, in FIG. 3 there is shown the forming blade 24, the anvil 20, the staple 34, the forming blade spring 28, and the anvil spring 26. Also there is an anvil upper stop 40a and lower stop 40b and a forming blade upper stop 42, and the anvil's lower tab 20t for receiving and engaging the lead staple from the cartridge. For convenience of references the anvil's upper stop 40a will also be designated as a basic starting reference plane R1 as a starting plane for the phases. In both FIGS. 3 and 4 the phases are designated 1-4a moving downward from top to bottom.

In FIG. 4 the activities of FIG. 3 have been separated into two columns A and C. More particularly, column A illustrates mainly the anvil 20 and staple 34 as they progress through the five stages; and column C illustrates the forming blade 24 and staple 34 as they progress through the stages. In column A the anvil has its upper stop 40a at reference plane R1, and a lower stop 40b; In column C the forming blade has its upper position at reference plane R2. At positions 2, 3, and 4 the anvil and forming blade have descended downward from their reference planes by distances corresponding to changes and locations of the staple as further described.

Beginning with phase or position 1 seen in FIGS. 3 and 4 and 4a and 4b, the anvil is located in its uppermost position defined by its upper stop 40a. With the anvil in this position, the engaged staple 34 is aligned with the lip 20t of the anvil, this staple having been automatically driven laterally into this position by the spring 38 of the magazine (shown in FIG. 2). In moving from position 1 to position 2 the forming blade 24 descends slightly to engage the top of the staple's crossbar while the bottom of the staple's crossbar is supported by the anvil's lower lip 20t. Subsequent downward movement by the forming blade will then be positively transferred by solid contact from the forming blade to the staple and the engaged anvil, thus moving all three parts simultaneously. FIGS. 4A and 4B correspond to FIG. 4 (column A) and FIG. 4 (column C) respectively and provide another perspective of the forming blade-anvil-staple relationship by illustrating a lateral spread of the relative elevation of these elements. During the succession of phases 1–4a discussed above, FIGS. 4A and 4B show the incremental distances moved by the anvil and forming blade between phases, while FIG. 4 shows schematically the cumulative distances moved from the initial reference planes $R_1$ and $R_2$ by these elements.

Figure 14:
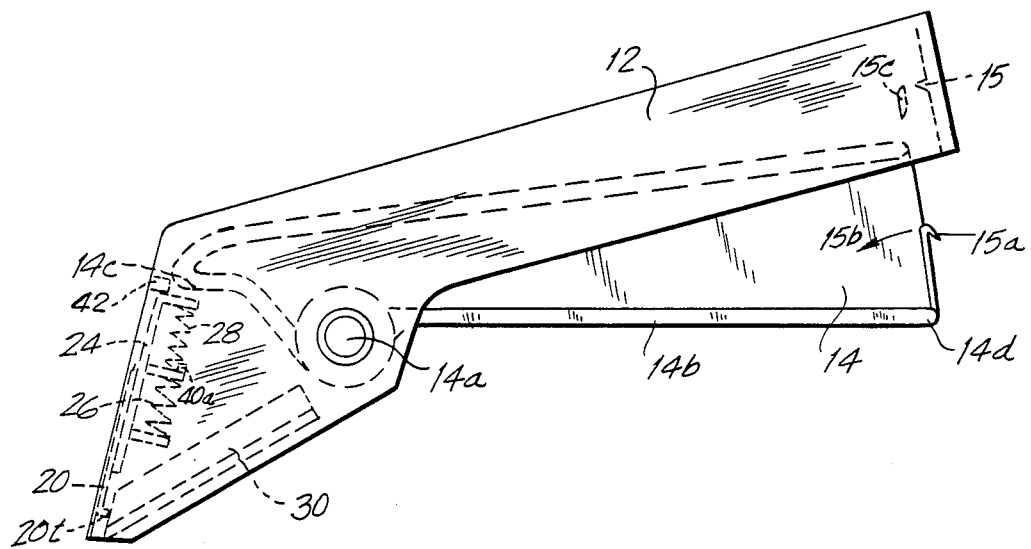
FIG. 14 is a side elevation view of the stapler of FIG. 1.

By appropriate designs of the springs 26 and 28, as seen in FIGS. 2, 3, and 14, the anvil is urged by spring 26 upward at all times relative to the casing, and having its upward motion limited by upper anvil stop 40a. The anvil is also urged toward the forming blade, and a separate spring 28 separates the forming blade from the anvil. When the operation of the stapler device proceeds from position 1 to 2 the staple is captured by virtue of the force of the forming blade applied toward the anvil which effectively sandwiches the staple therebetween, and thus captures it and prevents it from moving out of position or otherwise becoming displaced. The design of the springs is intended to produce about one pound of upward force between the anvil and the staple pushing up while the forming blade is correspondingly pushing down to thus securely hold the staple. It is intended for these elements to be loaded or preloaded in such a way that there is a net "up" force on the anvil, and that in the fully down position there will be sufficient "up" force to pull the forming blade off the staple and overcome the friction between the bottom of the forming blade and the top of the staple resulting after the staple has been bent into a closed position. If there isn't enough force urging the forming blade upward, i.e., if the spring is too soft, then there could be a hangup and the forming blade would in effect stick to the top of the staple and anvil and thus not rise.

A further review of FIGS. 3 and 4 will add certain perspective to the entire process. In FIG. 4, columns A and C the staple is shown initially in its partially closed position which is its shape as aligned on the mandrel in the cartridge 30 of FIG. 2. This staple shape, also seen in FIG. 6, is called herein "open configuration" since this is the staple's initial and most open shape. In phase 2 the forming blade descends slightly as indicated by the 0.027 inches. In position 3 the staple, while still open, has been pushed all the way down because the anvil has hit its lower stop 40b and the staple captured by the lower lip 20t of the anvil cannot descend any farther anyway. At position 4 the staple has been closed, and in position 4a the stripper, as further described below, strips the closed staple from the anvil, although the various elements are at the same elevation as before. At position 5 the anvil has ascended back to the original position leaving the staple closed and embedded in tissue; position 5 corresponds to position 1 so that the next lead staple will automatically be driven onto the anvil's lip 20t.

Column C illustrates how the forming blade moves downward from its reference level $R_2$ in position 1. At position 2 the forming blade has moved an amount indicated 0.027 inches as shown in in the drawing. At position 3 the forming blade is down 0.427 inches, at position 4 the forming blade has been driven another 0.08 inches to 0.507 inches in order to close the staple as shown, and by position 5 the forming blade has risen back to its reference position $R_2$.

The basic concept as described earlier includes use of a staple magazine or cartridge within the stapler housing where the magazine holds a plurality of staples in partially closed condition (called "open configuration"); one staple at a time it taken off the magazine, carried downward outside of the housing, caused to have its pointed ends pierce tissue, forced to bend to its closed condition, thereby being inserted in and gripping the tissue, and finally released from the stapler device.

In the preferred embodiment, a particular staple construction is used along with a staple delivery system as follows. FIG. 6 illustrates new generally symmetrical staple 34 in its initial "open" configuration, whose cross-section seen in FIG. 9 is essentially round along its full length, i.e., along the crossarm or arch 34a, the sides 34b, and the legs 34c, except for the points 34p. The points 34p are cut, sheared or ground at an angle of approximately 30° to insure maximum point sharpness. In the preferred embodiment the dimensions referred to in FIGS. 5–9 are $W_1 = 0.555''$, $0 = 25°$, $W_2 = 0.25''$ $r = 0.03''$, $H_1 = 0.173''$.

In the staple magazine the staples are aligned on a mandrel generally in the partially closed position seen in FIGS. 2, 6 and 17a which results in a delivery system being narrower than conventional systems, thereby contributing to improved visibility for the surgeon. As evident in FIG. 6 there is a gap 51 between the points 34p of the staple to allow a blade or stem of the mandrel to extend downward through the gap and be secured to the remaining part of the magazine.

FIGS. 2, 8, 17a and 17b illustrate the staple magazine and its operation. The mandrel 32 has an upper housing 32a with inner grooved surface 32b which helps guide the line of staples. The top surface 32c of the mandrel similarly guide the bottom and inner surface of the line of staples. As drawn the staples hang generally vertically relative to the inclined mandrel, and the lead staple 34A exits the mandrel off generally horizontal lip 33 and onto anvil lip 20t.

Figure 17:
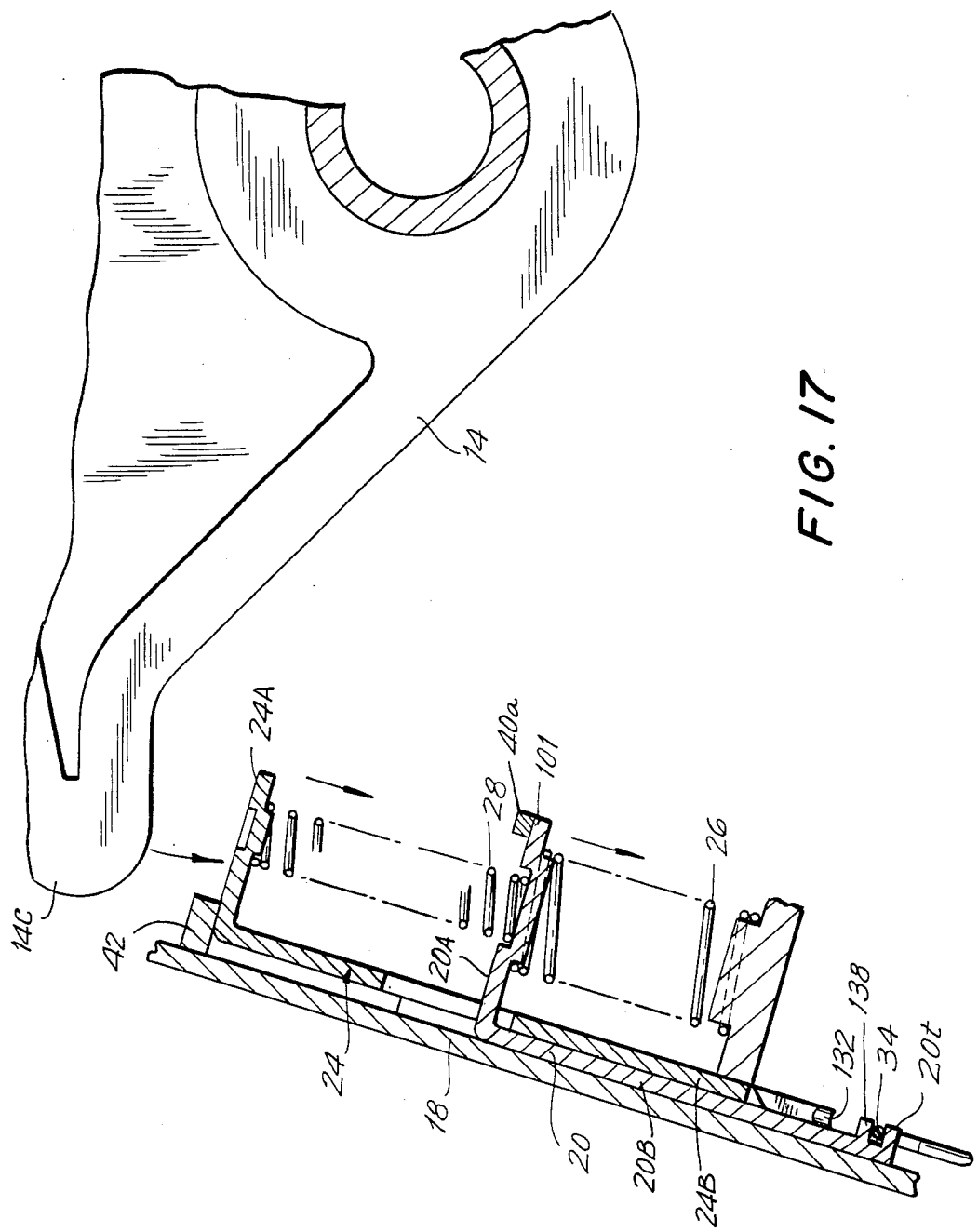
FIG. 17 is a fragmentary sectional view taken along line 17—17 of FIG. 1 of the staple-forming sub-assembly.

FIGS. 11, 17, 17a–17f, 19 and 19a further illustrate the staple delivery sub-assembly comprising the anvil 20 and the forming blade 24 in their relative positions. The anvil 20 has a generally vertical blade part with a lower lip 20t projecting rearwardly from the anvil blade into the plane of a staple 34. The anvil moves between upper and lower stops respectively fixed to the stapler housing as indicated in FIGS. 3 and 4. In the upper position the lower lip 20t of the anvil is positioned directly below the staple's crossbar or arch 34t as seen in FIG. 17b. The anvil spring 26 spring urges the anvil toward its upward position against stop 40a until the anvil is subsequently driven down in the staple delivery cycle.

When the anvil is stopped by the lower anvil stop, the forming blade overrides the interposed spring 28 and forces the staple sides 34s or top part 34t to bend around the ends of the anvil lip 20t and forces the legs 34l downward to pierce the skin. The spring 28, interposed between portions of the anvil and forming blade serves as a return spring for the forming blade urging it upward, as well as being an override spring which allows the forming blade to continue moving downward after the anvil 20 has moved to its lower position where its movement is restrained by the second or lower anvil stop.

FIG. 14 illustrates generally the stapler housing 12 in which the trigger 14 pivots about axis 14a. The trigger is pivoted by squeezing its gripping surface 14b, thus driving it in a counterclockwise direction and thereby urging its front end 14c to drive the forming blade 24 downward. As shown, the anvil spring 26 is stronger than interposed spring 28 between the forming blade and the anvil. Accordingly, pivoting of the trigger will cause the forming blade alone to descend initially; thereafter the forming blade and anvil will descend together, but by then the staple will be positively captured between them. At the bottom of the anvil's stroke, when it hits its stop 40b, the forming blade will then be driven further, overcoming its own return spring 28 as the staple is closed. The pivot point 14a of the trigger is situated much closer to the front end 14c of the trigger than the hand end 14b, thus providing a ratio greater than unity and a force advantage that allows the surgeon to deliver and form a staple with only a moderate amount of effort applied by his hand and fingers to the stapler trigger. FIG. 14 also shows symbolically the staple cartridge 30 positioned to deliver one staple at a time to the anvil. The last few degrees of motion of the forming blade cause the staple to be stripped.

Figure 19:
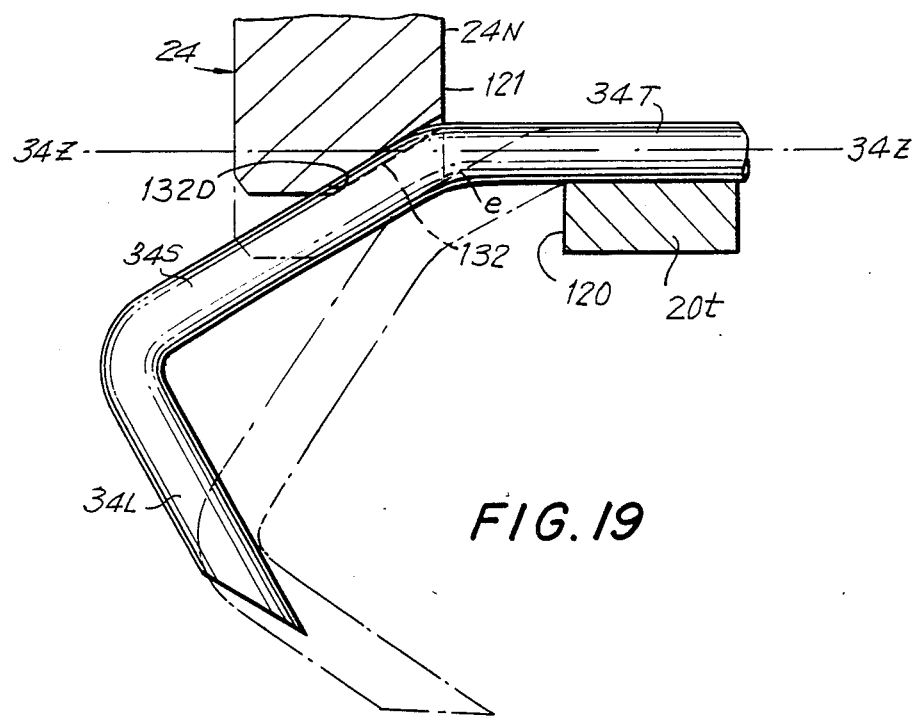
FIG. 19 and 20 are fragmentary front elevation views showing a staple in open, partially closed and fully closed states.
Figure 20:
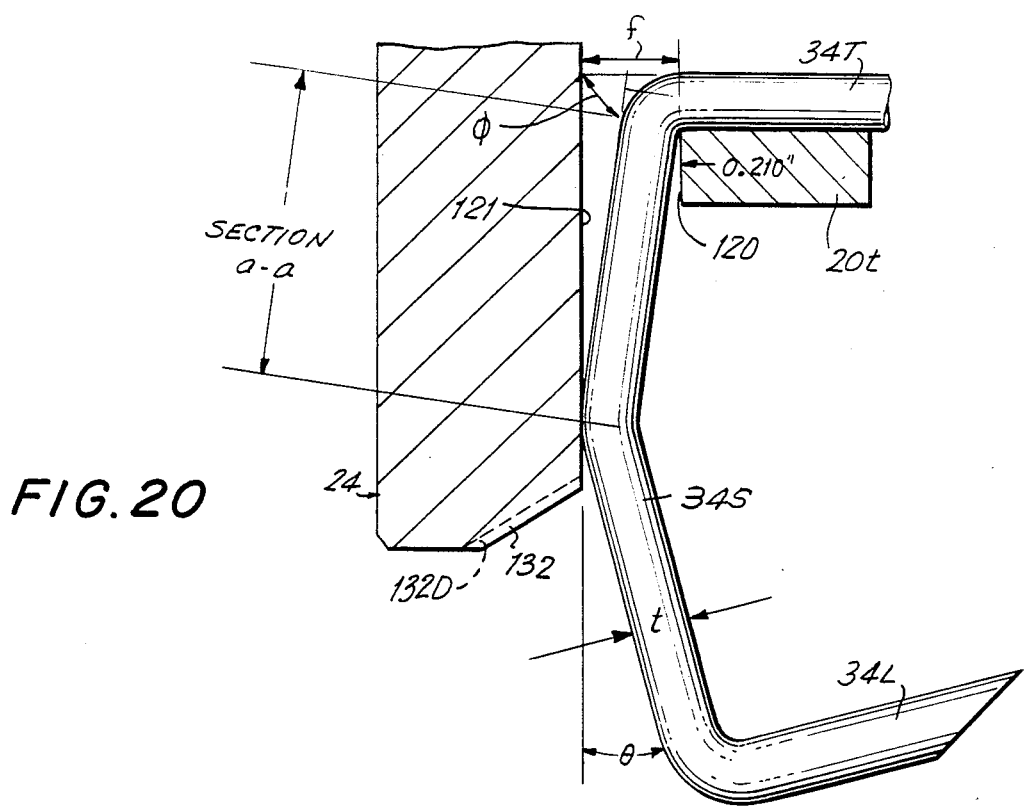

The actual closing of the staple by bending the opposite legs 34L is illustrated in FIGS. 19 and 20 as follows. When the staple is closed deformation occurs in the area marked "e" essentially because the anvil has a transverse dimension, in this case 0.210 inches which is substantially less than the original length of the horizontal crossarm 34T of the staple. During closure of the staple in the course of surgical insertion, the staple is closed by the forming blade which changes the staple from that shown in FIG. 6 to FIG. 7. The space on each side between the edge 120 of the anvil (FIGS. 19 and 20) and the adjacent inner edge 121 of the forming blade tine results in a gap within which the staple is bent. This gap, f in FIG. 20, is larger than the thickness of the staple t; in the embodiment shown f = 1.2t. The dimension f is significant because it represents the space allowed for the bent staple to exist; the more the staple is bent, the greater will be the friction between the two edges defining dimension f, and the more difficult it will be to effect closure and also the more difficult it will be to lift the forming blade away from and disengage from the staple which will be trapped between it and the anvil.

The prior art surgical staplers require approximately 55 lbs. of force to effect the bending because they have to bend essentially 90°, and this necessarily means that dimension f will be very small, in fact less than t, and the friction will be extremely high. In the present invention the force of only 18 pounds is required to achieve full closure or even to achieve overcrimping, i.e., closure until the staple legs are bent to the orientation illustrated in FIGS. 7 or 20 or 17f.

FIG. 19 illustrates a staple in its initial open phase 1 and an intermediate bent stage (shown in dotted line); FIG. 20 shows the staple in its final closed phase 4a. Also shown are the corresponding positions of the forming blade and the groove 132 in the forming blade which engages and guides the staple from tipping or rolling about any longitudinal axis 34Z extending through the crossbar. Point 132D of forming blade 24 is lower than axis 34Z, and the engagement of point 132D on the staple's side 34S stabilizes the staple from rolling or tipping about axis 34Z.

As the forming blade bends the staple around the corner of the anvil, the section of the staple between the corner of the anvil and the upper staple (Section a-a FIG. 20) corner rotates through an angle $\phi$ shown in FIG. 19 and 20. Due to the angle $\theta$ (see FIG. 6) between this section and the lower leg of the staple, the lower leg is rotated approximately 25 degrees ahead of the section a—a (see FIG. 20). Thus, to force the point 34P of the staple to rotate to a horizontal attitude requires a rotation $\phi$ of less than 90° of the staple leg 34L. A rotation of approximately 65 degrees will result in horizontal staple points, thus the dimension f in FIG. 20, which for a conventional stapler must be no wider than the wire thickness to ensure full rotation of the point, in this invention can be larger than the wire thickness (typically 1.2t). This results in a substantial reduction in the force required to close the staple which has important ramifications in other areas of the design. By reducing the dimension f, the points 34P of the staple when fully closed can be made to touch or cross providing overcrimp which significantly improves the staple's reliability of piercing the skin and thereafter remaining securely emplaced. Overcrimp means a staple configuration wherein the staple ends point slightly upward or overlie each other rather than merely point co-axially at each other while separated as seen in FIGS. 17f and 20.

Figure 11:
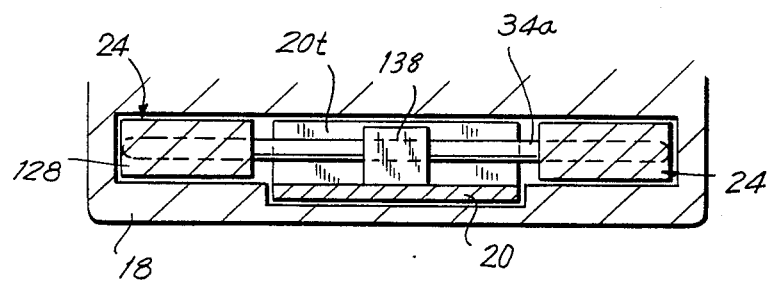
FIG. 11 is a fragmentary sectional view taken along line 11—11 of FIG. 1 of the staple-forming sub-assembly.

FIG. 11 is a sectional view corresponding to FIGS. 17 and 19A, showing the lateral relationship of the anvil, forming blade and front edge 18 of the housing. In FIG. 19A the anvil lip 20t has width $W_A$; W is the width of the open staple; WP is the width between staple points; d is the staple wire diameter; and as seen in FIGS. 19a and 20; 1.2d is the gap f between the anvil lip edge and the side wall 24N of the notch of the forming blade. Upon descent of the forming blade the staple is bent and the staple legs lie in the gap space.

The previously referred to detent and spring clip combination 15, 15a or equivalent device, provides an audible and/or physical indication that trigger movement has progressed a predetermined amount and the staple is in its lowest position ready for final closure. A second audible signal may be provided and indicate that closure has occurred, i.e., that the staple is fully closed and released from the device. Accordingly, with this feature the surgeon will know when he can still release the trigger, return the staple to the gun and attend to other matters prior to re-using. To an extent this apparatus is reversible in that the springs within the housing urge the pivoted trigger to return to its open position.

The stripper feature referred to earlier allows smooth and quick separation of the stapler from a staple after closure is complete and the staple legs are embedded in a patient's tissue. As indicated in FIGS. 3 and 4 stripping occurs between phases 4 to 4a, whereby the staple's crossbar is cammed off the anvil's lip. Details of the stripper are seen in FIGS. 17c–17f wherein the forming blade's lower edge or the throat 130 is beveled about 30°, while adjacent outer parts or tines 132 are grooved concavely. During initial phases of closure the forming blade's grooved edges 132 engage and partially capture the top outer edge of the staple's crossbar, such capture preventing the staple from "rolling" out of its essentially vertical plane. Rolling or tipping of the staple is not uncommon in prior art staples when the staple points meet resistance to penetration or when the user inadvertently moves the stapler transversely off the plane of the staple while the points have penetrated tissue and the crossbar is still secured to the anvil.

After forcible descent of the forming blade relative to the anvil causing full closure of the staple's legs, slight additional trigger movement causes final descent of the forming blade relative to the anvil whereby the bevelled edge 130 in FIGS. 17e and 17f cams the staple's crossbar 34T off the anvil's supporting lip 136. This simple finger movement on the trigger affects full release of the staple with no requirement of the surgeon moving his hand or the stapler laterally forward or backward and no danger of the staple being "hung-up" or otherwise stuck in the stapler. The stripper action also assures separation despite any tendency of the staple to remain engaged to adjacent edges 132 of the forming blade which previously forced the staple into its final configuration, especially after release of the trigger. The exact angle of the bevelled edge 132 may vary depending on the diameter and cross-section of the staple's crossbar, and the amount of trigger motion one desires for stripping versus the speed of stripping, a greater angle obviously requirement more motion but less force.

The anvil is provided with an anti-bowing tang 138 seen in FIGS. 17e and 17f to prevent the crossbar of the staple from bowing upward when the legs are bent downward. The forming blade has a corresponding recess 140 to allow space for tang 138 on the forming blade's descent. Bowing of the crossbar is undesirable, because such would be a distortion of the intended final configuration and result in less effective closure security.

FIG. 17b shows details of the staple cartridge where the mandrel 32 is inclined downward about 45° and has a lead edge 33 as a generally horizontal lip, so that the lead staple 34A approaches the anvil's support lip 20t aligned therewith instead of inclined thereto as seen in FIG. 17b. The preferred form of mandrel shown in FIG. 17b tends to avoid the drawing down of the number two staple 34A' by the descending forming blade immediately after the lead staple is picked up by the anvil.

In concluding, a number of features will be summarized and/or redescribed from a different perspective. Because the stripper cams the crossbar of a closed staple off the anvil lip by virtue of continued squeezing of the trigger, the closed staple is disengaged from the gun in an essentially non-directional manner. More specifically, the surgeon is not required to move or urge the staple gun in a particular lateral, vertical or inclined direction relative to the engaged tissue to achieve disengagement. It is further noteworthy that this stripper is integral with the forming blade, so that no additional parts are required to be made or assembled. The staple magazine is normally attached to the lower front of the housing by an upward movement into the recess provided. As seen in FIG. 17a the line of staples is guided between the surfaces 32b and 32c.

A key feature of this new device is the descending anvil which receives and guides the staple downward and then supports and stabilizes it during closure. Additional stabilization is provided by the forming blade and the housing. A principal benefit of having the staple lowered below the housing before closure is that the staple may be essentially fully visualized from in front, above and beside the gun before and during closure.

The detent feature illustrated in FIG. 14 allows the trigger to move reversibly until detent 15a which is spring biased leftward in the direction of arrow 15b, is cammed rightward by cam 15c forcing detent 15a to engage projection 15. After this engagement the trigger cannot reverse, but can only continue, which helps prevent a double staple feed and resultant hang-up. Upon full squeezing of the trigger and full closure and release of the staple, release of the trigger leads the resilient detent to return by and be cammed forward by cam 15c so that detent 15a and projection 15 will not engage. Later, upon repeat of the cycle detent 15a is again cammed rearward to engage element 15.

The invention described herein has focused upon certain preferred embodiments and features; it is intended, however, that numerous variations and equivalent embodiments be considered within the spirit and scope of the invention as set forth in the appended claims.

The invention described herein has focused upon certain preferred embodiments and features; it is intended, however, that numerous variations and equivalent embodiments be considered within the spirit and scope of the invention as set forth in the appended claims.

We claim:

1. A surgical stapler for use with at least one staple that is bendable from open to closed configuration, the stapler having a housing, a magazine for carrying and dispensing staples, an anvil with a staple-supporting lip, a forming blade with a drive edge for engaging and bending a staple on the anvil lip from its open to closed configuration, and a trigger movable between start and end positions for driving said forming blade, the improvement in combination therewith wherein said anvil is movable between a start position where its lip receives and supports a staple from said magazine and an end position where said anvil is displaced from the magazine, the stapler further comprising means resiliently urging said anvil constantly toward its start position, said forming blade as driven by said trigger being movable sequentially between (a) a start position corresponding to the anvil's start position, (b) an engage position where said drive edge of the forming blade engages and captures a staple on the anvil while the anvil remains at its start position, (c) a transport position where the forming blade, anvil and captured staple are driven to the anvil's end position with a staple captured between said lip and drive edge, the anvil's lip being constantly urged toward said drive edge of the forming blade by said means resiliently urging said anvil, and (d) a close position where said drive edge of the forming blade bends a captured staple about said lip to said closed configuration while said anvil remains at said anvil's end position.

2. A stapler according to claim 1 wherein said forming blade further comprises stripping means for separating a staple in closed configuration from said anvil.

3. A stapler according to claim 2 wherein said forming blade is drivable by said trigger from said close position to a strip position, and said stripping means comprises a portion of said forming blade that cams a staple in closed configuration off said anvil lip during motion of the forming blade from said close position to said strip position while said anvil remains stationary.

4. A stapler according to claim 1 in combination with a staple which comprises a continuous wire bendable from open to closed configuration, said stapler in upright orientation having a top crossbar with opposite ends, two sides depending downward from ends of the crossbar respectively, and two legs depending downward from ends of the sides respectively and terminating in pointed ends, said crossbar and sides having upper and lower surfaces, the sides of each staple in said open configuration diverging from each other and the legs of the staple converging toward each other.

5. A stapler according to claim 4 wherein said drive edge has a first portion for engaging the crossbar of a staple when situated on said anvil lip, and a second portion for engaging the sides of said staple, said second part being transversely displaced from said first part in the direction toward said anvil, whereby, when said forming blade is moved toward its engage position, a staple on said anvil lip will be engaged by said second part before said first part.

6. Apparatus according to claim 4 wherein the crossbar of each staple has a length $L_1$ and said anvil has a length $L_2$ which is less that $L_1$, said anvil has ends and is generally centered below the crossbar of a support staple, and said forming blade is adapted to bend said crossbar at points adjacent and corresponding to the ends of the anvil lip.

7. Apparatus according to claim 4 wherein said forming blade at its close position bends each side of the staple relative to the crossbar from which is depends, whereby said legs of the staple in its closed configuration extend toward each other and are slightly inclined upward toward the crossbar.

8. A stapler according to claim 4 wherein said anvil comprises a body part and said lip extends transversely therefrom, said anvil further comprises a projection situated above and spaced from said lip and extending similarly as said lip, the crossbar of a supported staple being received between said lip and projection, whereby the projection limits said crossbar from bowing upward when said staple legs are bent downward.

9. A stapler according to claim 4 wherein said forming blade and anvil have parallel and adjacent body parts and each has an arm extending similarly and transversely of its body part, said arms being generally parallel, said forming blade spring being situated between and engaging said arms urging said forming blade toward its start position, said anvil spring situated between said anvil arm and the housing.

10. A stapler according to claim 4 wherein each leg defines a generally 90° angle with the side of the staple from which it depends.

11. A stapler according to claim 4 wherein the crossbar of said captured staple redefines therethrough a longitudinal axis, said drive edge has a portion thereof which engages said staple sides at a location displaced transversely from said longitudinal axis, whereby said captured staple is generally stabilized from rolling, tipping or being displaced relative to said anvil during said movement of said forming blade from its engage to its close position.

12. A stapler according to claim 1 wherein said trigger has a drive part for engaging said forming blade, said trigger being urged to its start position by said forming blade when said forming blade is moved from its engage positon to its start position.

13. A stapler according to claim 1 further comprising means actuated by the trigger for preventing the anvil from receiving a second staple from the magazine before the supported staple on the anvil is bent to its closed configuration and stripped from the anvil.

14. A stapler according to claim 1 wherein said means resiliently urging said anvil is an anvil spring, and said stapler further comprises a forming blade spring engaging and constantly urging said forming blade toward its start position, thereby urging said drive edge away from said anvil lip for defining a space therebetween for said lip to receive a staple from said magazine when said forming blade and anvil are in their respective start positions.

15. A stapler according to claim 14 wherein said anvil spring is stronger than said forming blade spring whereby said forming blade spring will compress as said forming blade moves to its engage position while said anvil spring remains uncompressed.

16. A stapler according to claim 1 wherein said housing further comprises a forming blade stop for engaging and limiting movement of said forming blade when moved to its start position from its engage position.

17. A stapler according to claim 1 wherein said trigger movement and corresponding forming blade and anvil movement are reversible from their start positions to a pre-cock position of the forming blade just before forming a staple to its closed configuration, the stapler further comprising reversibility prevention means to prevent further reversibility of said trigger, forming blade and anvil after the pre-cock position is reached until the forming blade has continued its seqeuntial movement and reached its end position and the closed staple in closed configuration has been stripped off the anvil.

18. A stapler according to claim 17 wherein said reversibility prevention means comprises first and second elements on said housing and trigger respectively, one of said elements having a path of motion that will interfere with the other element when said trigger, forming blade and anvil reach said pre-cock position, one of said elements being spring biased to deflect in one direction only, allowing said elements to pass each other as said trigger and forming blade are moved further toward their end positions but preventing said elements from passing each other in the reverse direction until the staple in closed configuration is stripped off the anvil.

19. A stapler according to claim 1 wherein said housing further comprises a forming blade stop for engaging and limiting movement of said forming blade when moved to its start position from its engage position.

20. A stapler according to claim 11 wherein the first part of the drive edge of the forming blade defined a groove which is generally aligned with and engages said side of the staple on the anvil when said forming blade moves to its engage position, for inhibiting the staple from rolling, tipping or being displaced relative to the anvil lip.

21. Apparatus according to claim 1 wherein said magazine comprises an elongated mandrel having a longitudinal axis for carrying said plurality of staples in line with a lead staple exposed at the front of the line, said mandrel, when said stapler is oriented with the anvil and forming blade moving vertically, being inclined downward toward the anvil lip and terminating in a horizontally extending edge directed to said anvil lip and on which said lead staple is delivered to the anvil lip.

22. A stapler according to claim 1 wherein said anvil lip when reaching its end position locates the captured staple below said housing with legs and sides of the staple exposed and visible.

23. A surgical stapler for use with a magazine which can carry and dispense at least one staple which is bendable from open to close configuration, the stapler having a housing adapted to hold a magazine, an anvil with a staple-supporting lip, a forming blade with a drive edge for engaging and bending a staple on the anvil lip from its open to closed configuration, and a trigger movable between start and end position for driving said forming blade, the improvement in combination therewith wherein said anvil is movable between a start position with its lip positioned for receiving and supporting a staple from a magazine positioned in said housing and an end position where said anvil is displaced from the magazine in said housing. the stapler further comprising means resiliently urging said anvil constantly toward its start position, said forming blade as driven by said trigger being movable sequentially between (a) a start position corresponding to the anvil's start position, (b) an engage position where said drive edge of the forming blade engages and captures a staple on the anvil while the anvil remains at its start position, (c) a transport position where the forming balde, anvil and a captured staple are driven to the anvil's end position with a staple captured between said lip and drive edge, the anvil's lip being constantly urged toward said drive edge of the forming blade by said means resiliently urging said anvil and (d) a close position where said drive edge of the forming blade bends a captured staple about said lip to said closed configuration while said anvil remains at said anvil's end position.

24. A stapler according to claim 23 wherein said forming blade further comprises stripping means for separating a staple in closed configuration from said anvil.

25. In combination, a surgical stapler and a staple, said staple comprising a continuous wire bendable from open to closed configuration, said staple in upright orientation being generally symmetrical, having a top crossbar with opposite ends, two sides depending from said ends of the crossbar respectively, and two legs depending from ends of the sides respectively and terminating in pointed ends, the stapler having a housing, magazine for carrying and dispensing staples, an anvil with a staple-supporting lip, a forming blade having a drive edge for engaging and bending a staple on the anvil lip from its open to closed configuration and having stripping means, and a trigger movable between start and end positions for driving said forming blade, the improvement wherein said anvil is movable between a start position where its lip receives and supports a staple from said magazine and an end position where said anvil is displaced from the magazine, the stapler further comprising means resiliently urging said anvil constantly toward its start position, said forming blade as driven by said trigger being movable sequentially between (a) a start position corresponding to the anvil's start position, (b) an engage position where said drive edge of the forming blade engages and captures a staple on the anvil while the anvil remains at its start position, (c) a transport position where the forming blade, anvil and captured staple are driven to the anvil's end position with said staple captured between said lip and drive edge, the anvil's lip being constantly urged toward said drive edge of the forming blade by said means resiliently urging said anvil, (d) a close position where said drive edge of the forming blade bends said captured staple about said lip to said closed configuration while said anvil remains at said anvil's end positon, and (e) a strip position whereby said stripping means cams said staple in closed configuration off said anvil lip while said anvil remains stationary.

26. A stapler according to claim 25 wherein said staple in open configuration is generally symmetrical and each of said sides of the staple define an obtuse angle with said longitudinal axis.

27. A stapler according to claim 26, wherein the first part of the drive edge of the forming blade defines a groove which is generally aligned with and engages said sides of the staple on the anvil when said forming blade moves to its engage position, for inhibiting the staple from rolling, tipping or being displaced relative to the anvil lip.

28. A stapler according to claim 27 wherein said staple's crossbar defines therethrough a longitudinal axis, and wherein at least a portion of said first part of said drive edge engages said side of the staple at a location displaced transversely from said longitudinal axis, whereby said captured staple is generally stabilized from rolling or being displaced relative to said anvil during said movement of said forming blade from its engage to its close positions.

29. A stapler according to claim 26 wherein said drive edge surface comprises spaced apart tines and a throat therebetween which are said first and second parts respectively, and when the forming blade is in its engage position the tines engage the sides of the staple with the throat adjacent and transversely spaced from said crossbar.

30. A stapler according to claim 26 wherein said obtuse angle is in the range of 20° to 30°.

* * * * *

UNITED STATES PATENT AND TRADEMARK OFFICE
CERTIFICATE OF CORRECTION

PATENT NO. : 4,582,237

DATED : April 15, 1986

INVENTOR(S) : Anthony Storace, et al.

It is certified that error appears in the above-identified patent and that said Letters Patent is hereby corrected as shown below:

ABSTRACT, line 12, delete "and",(second occurrence)

Column 3, line 52, omit "an".

Column 5, line 6, change "tab" to -- lip --.

Column 5, line 22, after "of the" insert --descended --.

Column 7, line 40, change "34c" to -- 34L --.

Column 7, line 55, omit "8".

Column 10, line 8, omit "the".

Column 10, line 39, "requirement" to -- requires --.

Column 12, line 42, omit "is" and insert -- it --.

Column 12, line 66, omit "captured".

Column 12, line 66, omit "redefines" and insert -- defines --.

Column 13, line 2, omit "captured".

Column 13, line 65, change "defined" to -- defines --.

UNITED STATES PATENT AND TRADEMARK OFFICE
CERTIFICATE OF CORRECTION

PATENT NO. : 4,582,237

DATED : April 15, 1986

INVENTOR(S) : Anthony Storace, et al.

Page 2 of 2

It is certified that error appears in the above-identified patent and that said Letters Patent is hereby corrected as shown below:

Column 14, line 19, change "close" to -- closed --.

Column 16, line 9, change "side" to -- sides --.

Signed and Sealed this

Fourteenth Day of April, 1987

Attest:

DONALD J. QUIGG

*Attesting Officer*   *Commissioner of Patents and Trademarks*

UNITED STATES PATENT AND TRADEMARK OFFICE
CERTIFICATE OF CORRECTION

PATENT NO. : 4,582,237

DATED : April 15, 1986

INVENTOR(S) : Anthony Storace, et al

It is certified that error appears in the above-identified patent and that said Letters Patent is hereby corrected as shown below:

On the title page Insert

--(73) Assignee: Technalytics, Inc., Elmsford, N.Y.--.

Signed and Sealed this

Twenty-eighth Day of February, 1989

Attest:

DONALD J. QUIGG

*Attesting Officer*     *Commissioner of Patents and Trademarks*